United States Patent
Abdul Malak et al.

(10) Patent No.: US 6,790,454 B1
(45) Date of Patent: Sep. 14, 2004

(54) PROCESSES FOR THE PREPARATION OF NOVEL COLLAGEN-BASED SUPPORTS FOR TISSUE ENGINEERING, AND BIOMATERIALS OBTAINED

(75) Inventors: Nabil Abdul Malak, Caluire (FR); Valérie Andre, Ampuis (FR); Alain Huc, Ste.Foy les Lyon (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/616,526

(22) Filed: Jul. 14, 2000

(30) Foreign Application Priority Data

May 26, 2000 (FR) .............................. 00 06743

(51) Int. Cl.$^7$ .......................... A61F 13/00; A61F 2/00; A61F 2/10; A61K 38/17; C07K 1/00
(52) U.S. Cl. ...................... 424/422; 424/423; 424/424; 424/425; 623/15.12; 530/356
(58) Field of Search ................................ 424/422, 423, 424/424, 425; 530/356; 623/15.12

(56) References Cited

U.S. PATENT DOCUMENTS

| | | | |
|---|---|---|---|
| 5,093,474 | A | 3/1992 | Grossman et al. |
| 5,166,187 | A | 11/1992 | Collombel et al. |
| 5,264,551 | A | 11/1993 | Petite et al. |
| 5,273,900 | A | 12/1993 | Boyce |
| 5,331,092 | A | 7/1994 | Huc et al. |
| 5,412,076 | A | 5/1995 | Gagnieu |
| 5,420,248 | A | 5/1995 | Devictor et al. |

FOREIGN PATENT DOCUMENTS

| | | |
|---|---|---|
| DE | 226 153 A3 | 8/1995 |
| EP | 0 602 297 A1 | 6/1994 |
| EP | 0 753 313 A1 | 1/1997 |
| FR | 592603 A | 8/1925 |
| FR | 2 679 779 | 2/1993 |
| FR | 2 724 563 | 3/1996 |
| GB | 2 238 051 A | 5/1991 |
| WO | WO 90/12055 | 10/1990 |
| WO | WO 91/16010 | * 10/1991 |
| WO | WO 95 17428 | 6/1995 |
| WO | WO 96 08277 A1 | 3/1996 |
| WO | WO 97/20569 | 6/1997 |
| WO | WO 99 19005 A | 4/1999 |

OTHER PUBLICATIONS

International Search Report dated Feb. 28, 2001.
International Search Report dated Mar. 16, 2001.
Yeh et al "A Novel Native Matrix for Tissue Engineering Analysis of Cell–Matrix Interaction". Faseb Journal. vol. 14, No. 4, Mar. 15, 2000.
Derwent accession No. 1995–151478 & JP 07 075566 A. Marino Forum 21 SH, Mar. 20, 1995.
Wang et al. "Collagen Fibres with Improved Strength for the Repair of Soft Tissue Injuries" Biomaterials, vol. 15. No. 7 (1994): pp. 507–512.
Giraud–Guille et al. "Structural Aspects of Fish Skin Collagen whichh Forms Ordered Arrays via Liquid Crystalline States" Biomaterials, vo 21, No. 9 (May 2000) pp. 899–906.
French Search Report dated Feb. 2, 2000.
Chemical Abstracts. vol. 112, No. 8. Skrodzki et al. "Manufacture of aqueous collagen–containing solutions from fish skin." Feb. 18, 1990. XP–002127982.
Josephson et al. "Bisulfite Suppression of Fish Aromas."*Journal of Food Science*. vol. 48 (1983): pp. 1064–1067. XP002127981.
Patent abstracts of Japan. vol. 15. No. 275. JP 03–094633 (Ishiwatari). Apr. 19, 1991.
Boyce et al. "Structure of a Collagen–GAC Dermal Skin Substitute Optimized for Cultured Human Epidermal Keratinocytes". *Journal of Biomedical Materials Research*, vol. 22, 939–957 (1988).

* cited by examiner

*Primary Examiner*—Kenneth R. Horlick
*Assistant Examiner*—Teresa Strzelecka
(74) *Attorney, Agent, or Firm*—Merchant & Gould P.C.

(57) ABSTRACT

A composite product is disclosed as a collagen support comprising at least one porous collagen layer covered on at least one side with an essentially compact collagen membrane consisting either of a collagen film prepared by drying a collagen gel, preferably in air or a gaseous fluid, or of a very highly compressed collagen sponge. At least one of the two layers, i.e. the porous layer and the essentially compact membrane, may comprise normal, genetically modified or malignant living cells originating particularly from young or elderly subjects. This composite product is used as a collagen support for the manufacture of artificial skin intended especially for performing in vitro tests on the efficacy of potentially active substances or for reconstructing damaged areas of skin in vivo.

76 Claims, 2 Drawing Sheets

INVENTION

PROCESSES FOR THE PREPARATION OF NOVEL COLLAGEN-BASED SUPPORTS FOR TISSUE ENGINEERING, AND BIOMATERIALS OBTAINED

SUBJECT OF THE INVENTION

This invention relates to a composite product as a collagen support comprising at least one porous collagen layer covered on at least one side with an essentially compact collagen membrane consisting either of a collagen film prepared by trying a collagen gel, preferably in air or a gaseous fluid, or of a very highly compressed collagen sponge. This composite product may be used for the manufacture of artificial skin.

TECHNOLOGICAL BACKGROUND

For many years collagen has proved to be an irreplaceable substrate for the production of artificial tissues containing living cells.

The biomaterials obtained are increasingly used in the field of pharmaceutics and they appear to have a very promising future for the preparation of injured connective tissues or for gene therapy by allowing the introduction and survival of modified cells in a living organism.

Furthermore, for "in vitro" tests, the cosmetic and dermopharmaceutical industries are increasingly using reconstructed skin, especially since animal tests are used less and less in these disciplines.

It is for this reason that several research teams throughout the world have been endeavoring to develop collagen-based supports for the production of living artificial tissues such as skin, cartilage, bone, tendon or reconstructed cornea, so these novel biomaterials have numerous fields of application.

It should be noted that the principal studies carried out in the field covered by the invention are attributable mainly to the following teams: Yannas I., Collombel C., Tinois E., Boyce S., Eisenberg H., Bell E., Kuroyanagi Y., Maruguchi T., Hanthamrongwit M., Auger F. A. and Osborne C. S.; cf. U.S. Pat. No. 5,273,900, for example.

All these researchers use either collagen gels or collagen sponges, the latter being obtained by lyophilization.

The main difficulties to be overcome in the production of supports for the production of living artificial tissues are as follows: good mechanical strength, low sensitivity to temperatures around 37° C., biological properties favorable to cell development and metabolism, low susceptibility to enzymatic degradation and, finally, for certain applications and particularly reconstructed skin, preferably the presence of a bilayer structure in which one of the layers is as compact as possible the other is porous.

The researches carried out hitherto have not provided collagen supports which satisfactorily comply with all the constraints listed above.

PURPOSES OF THE INVENTION

The object of the present invention is to solve these problems which have remained shelved from both the technical and industrial points of view.

The present invention makes it possible to solve all these technical problems in a particularly simple, inexpensive manner applicable to the industrial scale, particularly in cosmetics, dermopharmaceutics or pharmaceutics.

SUMMARY OF THE INVENTION

According to a first feature, the present invention provides a novel composite product forming a collagen support comprising at least one porous collagen layer covered on at least one side with an essentially compact collagen membrane consisting either of a collagen film prepared by drying a collagen gel, preferably in air or a gaseous fluid, or of a very highly compressed collagen sponge.

According to yet another advantageous characteristic of the composite product of the invention, the collagen sponge is compressed at a pressure of at least about 50 bar, equivalent to about $50.10^5$ Pascals (Pa), and preferably of between 50 bar ($50.10^5$ Pa) and 200 bar ($200.10^5$ Pa), this compression optionally taking place at a temperature of between 20 and 80° C. and preferably of between 40° C. and 60° C.

According to one advantageous characteristic of this composite product, the collagen product is selected from collagen and a mixture of collagen with a polysaccharide, particularly a glycosaminoglycan, chitosan or a derivative thereof, cellulose or a derivative thereof, dextran or a derivative thereof, an alginate or a derivative thereof, or a carrageenan.

According to another advantageous characteristic of this composite product, at least one of the two layers of the latter, i.e. the porous layer and the essentially compact membrane, comprises normal, genetically modified or malignant living cells originating particularly from young or elderly subjects.

In one advantageous variant, the living cells are selected from the group consisting of fibroblasts, keratinocytes, melanocytes, Langerhans' cells originating from the blood, endothelial cells originating from the blood, blood cells, particularly macrophages or lymphocytes, adipocytes, sebocytes, chondrocytes, osteocytes, osteoblasts and Merkel's cells originating from the blood, said cells being normal, genetically modified or malignant.

According to yet another advantageous characteristic, the composite product contains normal, genetically modified or malignant fibroblasts in the porous layer and normal, genetically modified or malignant living cells on the surface of the compact membrane, said cells being selected particularly from keratinocytes, melanocytes, Merkel's cells originating from the blood, Langerhans' cells originating from the blood, sebocytes, cells originating from the blood, and nerve cells.

In yet another advantageous embodiment of the invention, it can be of particular value to prepare either "young" reconstructed skin using cells taken substantially exclusively from young subjects, or "aged" reconstructed skin obtained from cells taken substantially exclusively from elderly subjects. These models will make it possible to improve our knowledge of the skin ageing process and study the influence of active agents on this process.

In yet another advantageous embodiment of the invention, the essentially compact membrane is prepared prior to combination with the porous layer, preferably comprising a collagen sponge, in particular by preparing the membrane and depositing it on a collagen gel before the whole is frozen and lyophilized to give said composite product.

In yet another embodiment of the composite product according to the invention, the collagen sponge and/or the collagen film and/or the collagen membrane of said product comprise collagen of mammalian origin, particularly of bovine origin.

In yet another advantageous embodiment of the composite product according to the invention, at least one of the two layers of said product is produced from a collagen gel containing a mixture of soluble collagen and insoluble collagen, for example in the form of fibers.

In the case of the composite product according to the invention, the collagen can be type I and/or type III collagen.

According to a second feature, the present invention also covers a process for the manufacture of a composite product comprising at least one porous collagen layer covered on at least one side with an essentially compact collagen membrane,
wherein:
  a) first of all the essentially compact collagen membrane is prepared either by drying a first collagen gel, preferably in air or with the aid of a gaseous fluid, or by compressing a collagen sponge obtained by the freezing-lyophilization of a collagen gel;
  b) a second collagen gel is prepared separately;
  c) either the essentially compact membrane is deposited on the second collagen gel, or the second collagen gel is poured onto the essentially compact membrane; and finally
  d) the whole is frozen-lyophilized to give said composite product.

In one advantageous variant of this process, the collagen sponge used to prepare the compact membrane is compressed at a pressure of at least 50 bar (about $50.10^5$ Pa) and preferably of between 50 bar ($50.10^5$ Pa) and 200 bar ($200.10^5$ Pa).

The compression step advantageously takes place at a temperature of between 20 and 80° C. and preferably of between 40° C. and 60° C.

In another advantageous embodiment of this process, the collagen sponge and/or the collagen film and/or the collagen membrane are prepared using either collagen or a mixture of collagen with a polysaccharide, particularly a glycosaminoglycan, chitosan or a derivative thereof, cellulose or a derivative thereof, dextran or a derivative thereof, an alginate or a derivative thereof, or a carrageenan.

In another variant of the process, at least one of the two layers, or both layers, are crosslinked.

In one advantageous variant, the above-mentioned crosslinking is a physical crosslinking, particularly a thermal dehydration under vacuum, or TDH, or a chemical crosslinking, particularly with diphenylphosphorylazide, or DPPA, with an aldehyde such as glutaraldehyde, with carbodiimide or with succinimide.

In another advantageous variant of this process, a compound which favors cell development, particularly a growth factor and especially a cytokine or a chemokine, is added during manufacture.

In another advantageous embodiment of the process according to the invention, provision is made for a step for the introduction of normal, genetically modified or malignant living cells into at least one of the two layers.

In one advantageous variant, said living cells are selected from the group consisting of fibroblasts, keratinocytes, melanocytes, Langerhans' cells originating from the blood, endothelial cells originating from the blood, blood cells, particularly macrophages or lymphocytes, chondrocytes, osteocytes, particularly osteoblasts. Merkel's cells originating from the blood, sebocytes, adipocytes and nerve cells.

In one particularly advantageous embodiment of the invention, the process comprises introducing fibroblasts into the porous layer.

In a more preferred embodiment of the invention, the process comprises depositing living cells on the surface of the compact membrane, said cells being selected particularly from keratinocytes, melanocytes, Merkel's cells originating from the blood, Langerhans' cells originating from the blood, sebocytes, cells originating from the blood, and nerve cells.

In one variant of the process of the invention, the living cells are provided either by the sequential culture or by the concomitant culture of the different types of cells, these cells originating from culture or biopsy.

According to a third feature, the present invention also covers the use of the composite product forming a collagen support as defined above, or as obtained by the process defined above, or as resulting from the following description relating especially to the examples, for which every characteristic which appears to be novel compared with any state of the art is claimed as such in its function and in its generality, for the manufacture of artificial skin intended especially for performing in vitro tests on the efficacy of a potentially active substance or for reconstructing damaged areas of skin in vivo.

According to one advantageous characteristic, the artificial skin can be obtained either substantially exclusively from young cells or substantially exclusively from aged cells, in particular for studying the tissue ageing process, especially the skin ageing process, and optionally for testing the efficacy of active principles on this process.

The invention also covers any artificial skin comprising living cells obtained either substantially exclusively from young cells or substantially exclusively from aged cells, in particular for studying the tissue ageing process, especially the skin ageing process, and optionally for testing the efficacy of active principles on this process. Specific embodiments of this artificial skins comprise the composite product according to the instant invention as a best embodiment.

Thus it is seen that the invention provides a solution to the above-mentioned technical problems.

To obtain the strongest collagen materials, the inventors carried out more particularly the process described in U.S. Pat. No. 5,333,092 granted on 19 Jul. 1994. This technique affords a mixture of soluble and insoluble type I and type III native collagens which are very strong from the mechanical point of view and very resistant to enzymatic digestion. These last two characteristics may optionally be improved by any crosslinking technique or by the addition of substances which interact strongly with collagen and do not exhibit toxicity towards the cells. Furthermore, this collagen production process makes it possible virtually to eliminate the risk of biological contamination due to bacteria, viruses or prions.

For the case of supports intended for obtaining reconstructed skin, the inventors came to the idea of preparing bilayer materials by producing firstly the more compact layer and then the porous sponge. This methodology has the advantage of resulting in a much more compact surface layer than all those described hitherto. In particular, sponges compacted by high compression, or films, can therefore be fixed to porous matrices.

The use of the supports described above for tissue engineering applications involves the inoculation of living or genetically modified cells, it being possible for the cells to develop either inside the collagen support or on its surface.

The reconstructed living tissues obtained in this way can be used in numerous cosmetic, dermopharmaceutical or pharmaceutical applications as:
  "in vitro" models for simulating the effects of ingredients on cell metabolisms for the purpose of evaluating the efficacy and toxicity of raw materials or more complex formulations;

reconstructed tissues capable of overcoming the deficiencies of damaged tissues: skin, cartilage, bone, tendon, cornea; or living implants containing modified cells capable of overcoming certain deficiencies of the organism, particularly in the field of gene therapy.

BRIEF DESCRIPTION OF THE EXAMPLES AND OF THE DRAWINGS

Other objects, characteristics and advantages of the invention will become clearly apparent from the following explanatory description referring to various Examples of the invention, which are given simply by way of illustration and cannot therefore in any way limit the scope of the invention. As indicated previously, any characteristic in the Examples which appears to be novel compared with any state of the art is claimed in its function and in its generality, independently of the context of the Example. Moreover, Examples 6 to 13 constitute currently preferred embodiments of the composite products according to the invention which form a collagen support. Example 14 refers to comparative tests demonstrating the value of the composite products according to the invention as collagen supports for the manufacture of artificial skin intended especially for performing in vitro tests on the efficacy of a potentially active substance or for reconstructing damaged areas of skin in vivo.

Example 15 shows a test for the use of a composite product according to the invention which constitutes an artificial skin prepared from cells of young donors, compared with reconstructed skin obtained from cells of elderly donors, within the framework of a procedure for testing the efficacy of an active principle in order to study the skin ageing process, especially by quantification of the laminins produced.

Figure 1:
FIG. 1 shows a sectional view, after marking by conventional histological staining, of a composite product according to the present invention which has been produced from a porous lower layer of bovine collagen covered on the top side with an essentially compact upper collagen membrane consisting of a collagen film prepared by drying a collagen gel in air under the conditions of Example 6.
Figure 2:
FIG. 2 shows a similar section obtained with a simple porous matrix which has been prepared with the same bovine collagen gel, except that it has not been covered, i.e. under the conditions of Example 1, showing the presence of deep inclusions of keratinocytes not limited to the surface.
Figure 3:
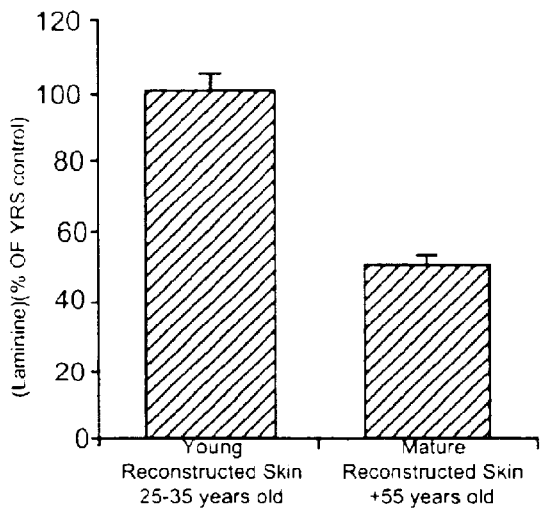
Figure 4:
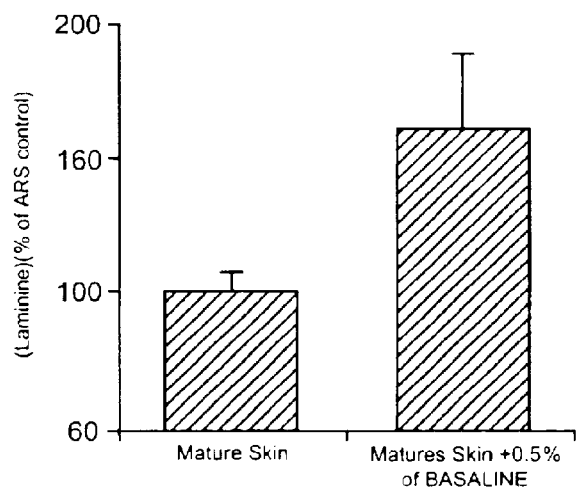
Figure 5:
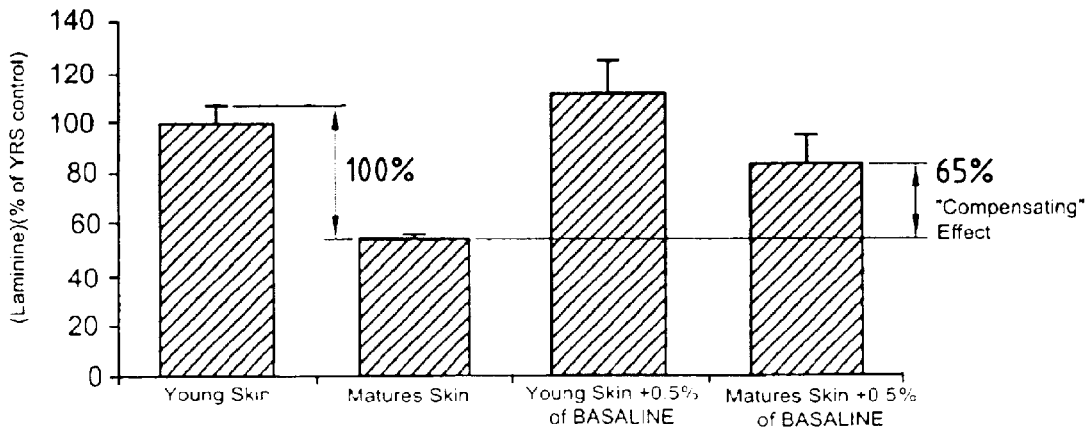

FIG. 3 shows the quantity of laminins present in the reconstructed skin incubation media, respectively for young reconstructed skin obtained from cells taken from donors of 25 to 35 years of age, and for mature or aged reconstructed skin obtained from cells taken from donors of more than 55 years of age, in order to show the influence of the donor's age, the results being expressed in the form of "bars" and the quantity of laminins produced being expressed on the ordinate as a percentage of the control (YRS=young reconstructed skin);

FIG. 4 shows the inductive effect of a fermented malt extract commercially available under the trade mark BASALINE®, COLETICA, France, on the production of laminins in mature reconstructed skin, the quantity of laminins produced again being expressed as a percentage of the control; and FIG. 5 shows the compensating effect of the same fermented malt extract, or BASALINE®, the quantity of laminins produced being expressed on the ordinate as a percentage of the control.

DETAILED DESCRIPTION OF THE INVENTION

EXAMPLE 1 OF THE INVENTION

Preparation of a porous matrix of native collagen by the technique of U.S. Pat. No. 5,331,092

A—Preparation of the Native Collagen

A gel is prepared from calf skins which have previously been washed (2 hours) and then depilated with a lime/sulfide mixture (lime: 3.5%, sodium sulfide: 2.5%) at a rate of 400 g of skin (solids content: about 30%) to 250 ml of water. This bath lasts for 30 minutes with rotation at 4 rpm.

The total depilation time is 36 hours.

The skins are then unlimed in a bath containing ammonium chloride (3%) and sodium metabisulfite (0.5%) at a rate of 400 g of skin to 50 ml of bath.

The total duration of this bath is 2 hours thirty minutes.

The salts are removed by two successive washes with water (15 minutes per wash) at a rate of 200 ml of water to 100 g of tissue.

The skins are subsequently ground and then washed by agitation for 1 hour with phosphate buffer of pH 7.8 (0.78 g/l of potassium dihydrogen-phosphate and 21.7 g/l of disodium monohydrogenphosphate) at a rate of 5 l buffer/kg ground material. The phosphate is then removed by two successive washes with softened water and then by continuous centrifugation at 4000 rpm (Rousselet centrifuge) at a rate of 5 l of water per kg of ground material.

The ground material is then acidified with 10% acetic acid solution, the amount of acetic acid being 5% based on the collagen; the final molarity is about 0.08 M.

The ground material is then malaxated for one hour to give a paste.

The gel is obtained by continuously passing the paste through a UTL T/-6 ultrasonic treatment apparatus. This gel has a concentration of between 0.7 and 2% of collagen, the proportion of acid-soluble collagen varying from 10 to 20% based on the insoluble collagen.

B—Preparation of the Porous Matrix with the Collagen Gel Obtained as Indicated Above 20 g/cm$^2$ of collagen gel (solids content=0.75%) are placed in a lyophilization tray and lyophilized by freezing at −30° C. and then heating at +32° C. The total lyophilization time is 16 hours under a pressure of 400 microbar.

The lyophilizate is crosslinked by a physical method (TDH), the lyophilizate being placed for 10 hours in an oven at 110° C. and 400 microbar of pressure.

EXAMPLE 2 OF THE INVENTION

Preparation of a porous matrix crosslinked with diphenylphosphorylazide (DPPA) by the technique described in European patent no. 466 829 of 24 Jul. 1996

The collagen lyophilizate is incubated for 24 h in a solution containing 5 to 250 μl DPPA/g collagen in 100 ml of dimethylformamide (DMF). The collagen is then rinsed in 100 ml of DMF to remove the DPPA. The DMF is then removed by rinsing in 100 ml of a borate buffer solution of pH 8.9 (0.04 M sodium tetraborate, 0.04 M boric acid).

The collagen is finally incubated overnight in the same borate buffer, the borate buffer then being removed by continuous rinsing with softened water for 6 h.

EXAMPLE 3 OF THE INVENTION
Preparation of a porous matrix crosslinked with carbodiimide and N-hydroxy-succinimide The collagen is crosslinked with EDC (ethyldimethylaminopropylcarbodiimide) at a concentration of 0.23 to 0.69 g/g collagen and with NHS (N-hydroxysuccinimide) at a concentration of 0 to 0.42 g/g collagen.

After rinsing with softened water, the collagen is lyophilized again.

EXAMPLE 4 OF THE INVENTION
Preparation of a porous matrix crosslinked with glutaraldehyde The collagen is crosslinked for 24 to 96 h in a solution containing 0.6 to 1% of GTA at 20° C.

After rinsing with softened water, the collagen is lyophilized again.

EXAMPLE 5 OF THE INVENTION
Porous matrix prepared with the native collagen of Example 1 in association with chitosan and a glycosaminoglycan as described in European patent no. 296078 of 29 May 1991

A solution of 2.5 g of chitosan in 356 ml of water and 1.9 ml of acetic acid, and then a solution containing 1 g of chondroitin 4-sulfate in 400 ml of softened water, are added to 600 g of 1.5% collagen gel. The mixture, which has a pH of about 4.0, is subsequently agitated and then lyophilized.

The sponge obtained is crosslinked by TDH.

EXAMPLE 6 OF THE INVENTION
Porous matrix described in Example 1, covered with a collagen film A—Preparation of the film Collagen gel with a solids content of between 0.3 and 0.8% is dried in an oven at 30° C. or under a hood at a rate of 0.5 g gel cm$^2$ tray.

10 to 40% of glycerol can be added to the collagen gel.

The collagen dried under these conditions forms a transparent film.

B—Association of the film with the porous matrix described above 0.5 g/cm$^2$ of collagen gel of example 1 with a solids content of 0.75% is placed in a lyophilization tray, the collagen film is then deposited on this gel and the whole is lyophilized.

The lyophilizate obtained is crosslinked by TDH.

EXAMPLE 7 OF THE INVENTION
Porous matrix prepared with an acid-soluble collagen gel and covered with a collagen film The process is that indicated in Example 6, the only difference being in the nature of the gel poured onto the film, which consists of acid-soluble collagen prepared by a technique well known to those skilled in the art.

EXAMPLE 8 OF THE INVENTION
Porous matrix prepared with an atelocollagen gel and covered with a collagen film The process is that indicated in Example 6, the only difference being in the nature of the gel poured onto the film, which consists of atelocollagen i.e. telopeptide-free collagen prepared by a technique well known to those skilled in the art.

EXAMPLE 9 OF THE INVENTION
Porous matrix consisting of collagen associated with chitosan and a glycosaminoglycan and covered with a collagen film The process is that indicated in Example 6 except that in this case the gel poured onto the collagen film consists of collagen, chitosan and a glycosaminoglycan. The preparation of this gel is described in Example 5.

EXAMPLE 10 OF THE INVENTION
All the porous matrices described above, covered with a collagen film, can be crosslinked by the techniques described in Examples 2, 3 and 4.

EXAMPLE 11 OF THE INVENTION
Porous matrix of collagen only, described in Example 1, covered with a compressed collagen sponge A—Preparation of the compressed sponge Collagen gel prepared as in Example 1, with a solids content of between 0.3 and 1.5%, is lyophilized to give a sponge weighing between 0.5 and 2 g/cm$^2$.

The lyophilizate is compressed for 5 to 60 seconds at a temperature of between 20 and 60° C. and a pressure of between 50 and 200 bar (50 to 200.10$^5$ Pa).

B—Association of the compressed sponge with the porous matrix

The collagen gel described in Example 1 is deposited in a lyophilization tray at a rate of 0.5 g per cm$^2$. The compressed sponge is then deposited on this gel and the whole is lyophilized to give a porous collagen sponge covered with a compressed collagen sponge. The whole is crosslinked by TDH as described in Example 1.

EXAMPLE 12 OF THE INVENTION
Porous matrix consisting of collagen, chitosan and glycosaminoglycan, as described in Example 5, covered with compressed sponge The collagen, chitosan and glycosaminoglycan gel prepared by the process of Example 5 is deposited in a lyophilization tray at a rate of 0.5 g per cm$^2$, the compressed sponge is then deposited on this gel and the whole is lyophilized. The lyophilizate is then crosslinked by TDH as described in Example 1.

EXAMPLE 13 OF THE INVENTION
All the porous matrices described above, covered with a compressed collagen sponge, can be crosslinked by the techniques described in Examples 2, 3 and 4.

EXAMPLE 14 OF THE INVENTION
Reconstructed skin prepared either with the aid of the DPPA-crosslinked porous matrix described in Example 2, or with the aid of the DPPA-crosslinked porous matrix of Example 2 covered with a compressed collagen sponge, the whole being crosslinked with DPPA, according to Example 13, in order to allow a comparison to be made between a composite product comprising a porous collagen layer covered with an essentially compact membrane according to the invention and a product comprising a porous collagen layer only, with no covering Preparation of Reconstructed Skin a) Culture of Normal Human Fibroblasts Normal human fibroblasts taken arbitrarily from elderly or young subjects are used; they are recovered and developed in a manner conventional to those skilled in the art for recovery between the sixth and tenth passages.

Inoculation is carried out at a rate of 250,000 cells per cm² of porous matrix, the latter being either the comparison product comprising only the DPPA-crosslinked porous matrix of Example 2, or the composite product according to the invention comprising the DPPA-crosslinked porous matrix of Example 2 covered with a compressed collagen sponge, the whole being crosslinked with DPPA, according to Example 13.

The culture medium is composed of DMEM/HAM F12 50/50 (v/v) supplemented with 10% by weight of fetal calf serum, 100 IU/ml of penicillin, 25 µg/ml of gentamycin, 1 µg/ml of amphotericin B and 50 µg/ml of vitamin C.

Culture is carried out for three weeks, the medium being changed three times a week.

b) Culture of Normal Human Keratinocytes

Normal human keratinocytes obtained arbitrarily from young or elderly subjects are then cultured; they are recovered and cultivated by the culture techniques well known to those skilled in the art for recovery between the first and third passages.

Inoculation is carried out at a rate of 250,000 cells per cm² of surface, which is either the surface of the DPPA-crosslinked porous matrix of Example 2, or the surface of the composite product according to the invention comprising the DPPA-crosslinked porous matrix of Example 2 covered with a compressed collagen sponge, the whole being crosslinked with DPPA, according to Example 13, in which case the keratinocytes are inoculated onto the surface of the essentially compact collagen membrane.

The culture of these products, comprising an inoculation of both fibroblasts and keratinocytes, takes place in a Green's medium composed of:

DMEM supplemented with:
30% of HAM F12,
10% of fetal calf serum,
100 IU/ml of penicillin,
100 µg/ml of streptomycin,
1 µg/ml of amphotericin B,
2 µmol/ml of L-glutamine,
10 ng/ml of EGF (Epidermal Growth Factor),
0.12 IU/ml of insulin commercially available under the trade mark UMULINE®,
400 ng/ml of hydrocortisone,
$10^{-12}$ mol/ml of cholera toxin,
5 µg/ml of transferrin,
$2.10^{-9}$ M triiodothyronine,
$1.8.10^{-7}$ mol/ml of adenine,
50 µg/ml of vitamin C.

This culture is carried out for one week, the media being changed every day.

c) Culture of the Composite Product According to the Invention and the Comparative Non-covered Porous Layer After the culture of step b) has been carried out for one week with the media being changed every day, the surface layer containing the keratinocytes is caused to emerge at the air-liquid interface, while the layer containing the fibroblasts remains immersed, and culture is then carried out for three weeks in an emersion medium composed of:

DMEM supplemented with:
10% of fetal calf serum,
100 IU/ml of penicillin,
100 µg/ml of streptomycin,
1 µg/ml of amphotericin B,
2 µmol/ml of L-glutamine,
10 ng/ml of EGF,
0.12 IU/ml of insulin of trade mark UMULINE®,
400 ng/ml of hydrocortisone,
50 µg/ml of vitamin C.

The total culture time of 7 weeks resulting from steps a) to c) gives a reconstructed skin composed of a reconstructed dermis, the fibroblasts having colonized the three-dimensional collagen matrix, said dermis being covered with a multilayer epidermis.

The dermo-epidermal interface shows the presence of a basal membrane in which it is possible to identify the presence of laminin-1, laminin-5, type IV collagen and type VII collagen by immunolabeling.

Thus, after three weeks of preparation of the dermis equivalent, covering of the porous matrices with an essentially compact layer to give a composite product according to the invention affords a greater quantity of fibroblasts on the surface of the collagen matrices before epidermization.

In the case of a porous matrix only, i.e. with no covering, if the surface layer of fibroblasts is not completely contiguous, keratinocytes can infiltrate the underlying dermis equivalent and form islets of keratinocytes, which are totally abnormal features.

Thus it is seen that the invention, which uses more compact layers than those previously available for use in the prior art, provides better security against the penetration of keratinocytes.

It is pointed out that the abbreviation DMEM in the description denotes Dulbecco Modified Eagle's Medium.

EXAMPLE 15 OF THE INVENTION

Study Comparing Skin Reconstructed from Cells of Young Donors and Skin Reconstructed from Cells of Elderly Donors with the Composite Products According to the Present Invention in Order to Measure the Efficacy of Active Principles on the Production of Laminins The procedure in this Example is essentially as described in Example 14 as regards the cultures, using the same composite product according to the present invention comprising a DPPA-crosslinked porous collagen layer or matrix described in Example 2, covered with a compressed collagen sponge, the whole being crosslinked with DPPA, according to Example 13. The procedure is as follows:

1) Preparation of the Reconstructed Skin

Young reconstructed skin was prepared by the procedure described in Example 14 except that the fibroblasts and keratinocytes originated respectively from young donors, i.e. those of between 25 and 35 years of age. Also, aged or mature reconstructed skin was obtained by using fibroblasts or keratinocytes originating from elderly donors of more than 55 years of age.

a) Materials and Method

As indicated in Example 14, step a, porous matrices of the composite product of the invention were first inoculated with normal human dermal fibroblasts originating either from pools of young cells or from pools of mature or aged cells, and culture is carried out for 21 days under the conditions described in Example 14, step a.

b) After the above-mentioned 21 days of culture, epidermal layers prepared separately from keratinocytes originating either from pools of young cells or from pools of mature cells are inoculated onto the surface of the essentially compact collagen membrane of the composite product.

Culture is carried out for 14 days under the conditions described in Example 14b.

2) Quantification of the Laminins

After the 14 days of culture of the fibroblast-keratinocyte composite, the laminins contained in the incubation media of the resulting young or mature reconstructed skin are quantified with the aid of a commercially available ELISA kit (Takara, Japan).

These results are reported in FIG. 3.

FIG. 3 shows that the mature reconstructed skin contains about half as much laminins as the young reconstructed skin (YRS) used as 100% control.

3) Measurement of the Inductive Effect of an Active Principle, Such as a Fermented Malt Extract Marketed by COLETICA Under the Trade Mark BASALINE®, on the Production of Laminins in Young and Mature Reconstructed Skin In this comparative test, the procedure is as described above except in regard to the 14 days of culture with keratinocytes; the young or mature reconstituted skin is maintained in culture for 14 days either in the absence (control) or in the presence of 0.5% by weight of fermented malt extracts commercially available under the trade mark BASALINE®, COLETICA, France.

At the end of the incubation period, as in the above Example, the laminins contained in the incubation media were quantified by ELISA.

The results are reported in FIG. 4.

The 100% control consists of the proportion of laminins in Aged Reconstructed Skin, or ARS.

FIG. 4 shows that the active principle extracted from fermented malt, or BASALINE®, was capable of stimulating laminin production in mature reconstructed skin. Under the same conditions, the active principle extracted from fermented malt, or BASALINE®, does not significantly modify laminin production in young reconstructed skin, as indicated in FIG. 5.

Thus it is seen that the active principle extracted from fermented malt, or BASALINE®, increases laminin production in mature reconstructed skin by 65%.

By the same token, this active principle does not affect the physiological processes involved in the regulation of laminin production in young reconstructed skin.

These experiments made it possible to evaluate the magnitude of the compensating effect of the fermented malt extract, or BASALINE®, defined as the capacity of this active principle to reduce the relative difference observed between laminin production in young reconstituted skin and that in mature reconstituted skin.

FIG. 5 shows that the difference between laminin production in young reconstituted skin and that in mature reconstituted skin can be reduced by 65% when the active principle is used at 0.5%.

What is claimed is:

1. A composite acellular product forming a collagen support comprising at least one porous collagen layer covered on at least one side with a collgen membrane prepared by a compression of a collagen sponge at a pressure of at least about 50 bar.

2. The product of claim 1, wherein the collagen of at least one of the porous layer and of the collagen membrane is selected from the group consisting of collagen and a mixture of collagen with at least one polysaccharide selected from the group consisting of a cellulose, a dextran, an alginate, a carrageenan a glycosaminoglycan, and a chitosan.

3. A composite product comprising the composite acellular product of claim 1, wherein at least one of the porous layer and of the collagen membrane, comprises living cells selected from the group consisting of normal living cells, genetically modified living cells and malignant living cells.

4. The product of claim 3, wherein said living cells originate from young subjects.

5. The product of claim 3, wherein said living cells originate from elderly subjects.

6. The product of claim 3, wherein said living cells are selected from the group consisting of fibroblasts, keratinocytes, melanocytes, Langerhans' cells originating from the blood, endothelial cells originating from the blood, blood cells, sebocytes, chondrocytes, osteocytes, osteoblasts and Merkel's cells, said cells being normal, genetically modified or malignant.

7. A composite skin product forming a collagen support comprising at least one porous collagen layer covered on at least one side with a collagen membrane prepared by a compression of a collagen sponge at a pressure of at least about 50 bar, said porous collagen layer comprising living fibroblasts and said collagen membrane comprising on the surface thereof living cells selected from the group consisting of: keratinocytes, melanocytes, Merkel's cells, Langerhans' cells originating from the blood, sebocytes, blood cells.

8. The product of claim 7, wherein the collagen sponge is compressed at a pressure of at least about 50 bar, and at a temperature ranging between about 20° C. and 80° C.

9. The product of claim 7, wherein the collagen sponge is compressed at a pressure between about 50 bar and 200 bar and at a temperature between about 40° C. and 60° C.

10. The product of claim 6, wherein the collagen membrane is prepared prior to combination with the porous layer.

11. The product of claim 6, further comprising a collagen gel on at least one surface of the membrane.

12. A composite acellular product forming a collagen support comprising at least one porous collagen layer covered on at least one side with a collagen membrane prepared by a compression of a collagen sponge at a pressure of at least about 50 bar, and wherein at least one of the porous layer and membrane is produced from a collagen gel containing a mixture of soluble collagen and insoluble collagen.

13. The product of claim 12, wherein said insoluble collagen comprises collagen fibers.

14. The product of claim 1, wherein at least one of said porous collagen layer and said collagen membrane is produced from a collagen gel containing a mixture of soluble collagen and insoluble collagen, wherein the collagen is selected from the group consisting of type I collagen and type III collagen.

15. An artificial skin comprising a product as defined in claim 1, 3, 7, or 12.

16. The artificial skin of claim 15, comprising living cells obtained from young subjects.

17. The artificial skin of claim 15, wherein said artificial skin comprises living cells obtained from elderly subjects.

18. The artificial skin of claim 15, comprising living cells selected from the group consisting of fibroblasts, keratinocytes, melanocytes, Langerhans' cells originating from the blood, endothelial cells originating from the blood, blood cells, sebocytes, chondrocytes, osteocytes, osteoblasts and Merkel's cells, said cells being normal, genetically modified or malignant.

19. The artificial skin of claim 18, wherein said blood cells are selected from the group consisting of macrophages and lymphocytes.

20. The artificial skin of claim 16, wherein at least one of said porous collagen layer and said collagen membrane comprises a compound which favors cell development.

21. The artificial skin of claim 20, wherein said compound which favor cell development is selected from the group consisting of a growth factor, cytokine and a chemokine.

22. The artificial skin of claim 15, wherein the collagen is selected from the group consisting of collagen and a mixture of collagen with at least one polysaccharide selected from the group consisting of a cellulose, a dextran, an alginate, a carrageenan, a glycosaminoglycan, and a chitosan.

23. The artificial skin of claim 15, wherein at least one of said porous collagen layer and said collagen membrane is crosslinked.

24. The artificial din of claim 23, wherein crosslinking is a thermal dehydration under vacuum.

25. The artificial skin of claim 23, wherein crosslinking is a chemical crosslinking selected from the group consisting of a crosslinking with diphenyl phosphorylaxide, crosslinking with an aldehyde, crosslinking with glutaraldehyde, a crosslinking with a carbodihymide, a crosslinking with a succinimide and combinations thereof.

26. A method of reconstructing damaged areas of skin in vivo comprising performing said reconstruction with an artificial skin prepared from a product selected from the group consisting of a composite product as defined in claim 3, 7, or 12.

27. The method of claim 26, wherein at least one of the porous layer and of the collagen membrane is produced from a collagen gel containing a mixture of soluble collagen and insoluble collagen, the collagen being selected from the group consisting of type I collagen and type III collagen.

28. The method of claim 26, wherein said artificial skin comprises living cells obtained from young subjects.

29. The method of claim 26, wherein said artificial skin comprises living cells obtained from elderly subjects.

30. The method of claim 26, comprising adding to at least one of the porous layer and of the collagen membrane living cells selected from the group consisting of fibroblasts, keratinocytes, melanocytes, Langerhans' cells originating from the blood, endothelial cells originating from the blood, blood cells, sebocytes, chondrocytes, osteocytes, osteoblasts, and Merkel's cells, said cells being normal, genetically modified or malignant.

31. The method of claim 30, wherein said blood cells are selected from the group consisting of macrophages and lymphocytes.

32. A method of in vitro testing of the efficacy of a potentially active substance comprising monitoring the effect of said potentially active substance on an artificial skin prepared from a composite product as defined in claim 3, 7, or 12, wherein said artificial skin comprises living cells obtained from young subjects.

33. A method of in vitro testing of the efficacy of a potentially active substance comprising monitoring the effect of said potentially active substance on an artificial skin prepared from a composite product as defined in claim 3, 7, or 12, wherein said artificial skin comprises living cells obtained from elderly subjects.

34. A composite acellular product forming a collagen support comprising at least one porous collagen layer covered on at least one side with a collagen membrane comprising a collagen film prepared by drying a collagen gel separately from the porous collagen layer.

35. The product of claim 34, wherein the collagen of at least one of the porous layer and of the collagen membrane is selected from the group consisting of collagen and a mixture of collagen with at least one polysaccharide selected from the group consisting of a cellulose, a dextran, an alginate, a carrageenan, a glycosaminoglycan, and a chitosan.

36. A composite product comprising the composite acellular product of claim 34, wherein at least one of the porous layer and of the collagen membrane, comprises living cells selected from the group consisting of normal cells, genetically modified living cells and malignant living cells.

37. The product of claim 36, wherein said living cells originate from young subjects.

38. The product of claim 36, wherein said living cells originate from elderly subjects.

39. The product of claim 36, wherein the living cells are selected from the group consisting of fibroblasts, keratinocytes, melanocytes, Langerhans' cells originating from the blood, endothelial cells originating from the blood, blood cells, sebocytes, chondrocytes, osteocytes, osteoblasts, and Merkel's cells, said cells being normal, genetically modified or malignant.

40. An artificial skin product forming a collagen support comprising at least one porous collagen layer covered on at least one side with a collagen membrane prepared by drying a collagen gel separately from the porous collagen layer, said porous collagen layer comprising living fibroblasts and said collagen membrane comprising on the surface thereof living cells selected from the group consisting of: keratinocytes, melanocytes, Merkel's cells, Langerhans' cells originating from the blood, and sebocytes.

41. The product of claim 40, wherein the collagen membrane is prepared by drying the collagen gel in air.

42. The product of claim 41, further comprising a collagen gel on at least one surface of the collagen membrane.

43. A composite acellular product forming a collagen support comprising at least one porous collagen layer covered on at least one side with a collagen membrane prepared by drying a collagen gel separately from the porous collagen layer, and wherein at least one of the porous layer and of the collagen membrane is produced from a collagen gel containing a mixture of soluble collagen and insoluble collagen.

44. The product of claim 43, wherein said insoluble collagen comprises collagen fibers.

45. The product of claim 34, wherein at least one of the porous layer and of the collagen membrane is produced from a collagen gel containing a mixture of soluble collagen and insoluble collagen, wherein the collagen is selected from the group consisting of type I collagen and type III collagen.

46. An artificial skin comprising a product selected from a product as defined in claim 34, 36, 40, or 43.

47. The artificial skin of claim 46, comprising living cells obtained from young subjects.

48. The artificial skin of claim 46, comprising living cells obtained from elderly patients.

49. The artificial skin of claim 46, comprising living cells selected from the group consisting of fibroblasts, keratinocytes, melanocytes, Langerhans' cells originating from the blood, endothelial cells originating from the blood, blood cells, sebocytes, chondrocytes, osteocytes, osteoblasts, and Merkel's cells, said cells being normal, genetically modified or malignant.

50. The artificial skin of claim 49, wherein said blood cells are selected from the group consisting of macrophages and lymphocytes.

51. The artificial skin of claim 46, wherein at least one of the porous layer and of the collagen membrane comprises a compound which favors cell development.

52. The artificial skin of claim 51, wherein said compound which favors cell development is selected from the group consisting of a growth factor, cytokine and a chemokine.

53. The artificial skin of claim 46, wherein the collagen is selected from the group consisting of a collagen and a mixture of collagen with at least one polysaccharide selected from the group consisting of cellulose, dextran, alginate, carrageenan, sulfated glycosaminoglycans, and chitosan.

54. The artificial skin of claim 46, wherein at least one of the porous layer and of the collagen membrane is crosslinked.

55. The artificial skin of claim 54, wherein crosslinking is a thermal dehydration under vacuum.

56. The artificial skin of claim 54, wherein crosslinking is a chemical crosslinking selected from the group consisting of a crosslinking with diphenyl phosphorylazide, crosslinking with an aldehyde, crosslinking with glutaraldehyde, a crosslinking with a carbodiimide, a crosslinking with a succinimide and combinations thereof.

57. An artificial skin product forming a collagen support comprising at least one porous collagen layer covered on at least one side with a collagen membrane comprising a collagen film prepared by drying a collagen gel in air separately from the porous collagen layer, said porous collagen layer comprising living fibroblasts cells and said collagen membrane comprising on the surface thereof living cells other than fibroblasts.

58. The product of claim 57, wherein said living cells on the surface of the membrane are selected from the group consisting of keratinocytes, melanocytes, Merkel's cells, Langerhans' cells originating from the blood, sebocytes, and blood cells.

59. The product of claim 57, wherein said living cells on the surface of the membrane comprise keratinocytes.

60. A method of reconstructing damaged areas of skin in vivo comprising performing said reconstruction with an artificial skin prepared from a product selected from the group consisting of a composite product as defined in claim 36, 40, 43, or 57.

61. The method of claim 60, wherein at least one of the porous layer and of the collagen membrane is produced from a collagen gel containing a mixture of soluble collagen and insouble collagen, the collagen being selected from the group consisting of type I collagen and type III collagen.

62. The method of claim 60, wherein said artificial skin comprises living cells obtained from young subjects.

63. The method of claim 60, wherein said artificial skin comprises living cells obtained from elderly subjects.

64. A method of in vitro testing of the efficacy of a potentially active substance comprising monitoring the effect of said potentially active substance on an artificial skin prepared from a composite product as defined in claim 36, 40, 43 or 57, wherein said artificial skin comprises living cells obtained from young subjects.

65. A method of in vitro testing of the efficacy of a potentially active substance comprising monitoring the effect of said potentially active substance on an artificial skin prepared from a composite product as defined in claim 36, 40, 43, or 57, wherein said artificial skin comprises living cells obtained from elderly subjects.

66. The product of claim 7, wherein said product is a reonstructed dermis, comprising the fibroblasts that colonized the porous collagen layer forming a three dimensional matrix, said dermis being covered with a multilayer epidermis comprising said collagen membrane.

67. The product of claim 40, wherein said product is a reconstructed skin composed of a reconstructed dermis, comprising fibroblasts that colonized the porous collagen layer forming a three dimensional matrix, said dermis being covered with a multilayer epidermis comprising said collagen membrane.

68. The product of claim 57, wherein said product is a reconstructed skin composed of a reconstructed dermis, comprising the fibroblasts that colonized the porous collagen layer forming a three dimensional matrix, said dermis being covered with a multilayer epidermis comprising said collagen membrane.

69. A method of reconstructing damaged areas of skin in vivo comprising performing said reconstruction with an artificial skin prepared from a product selected from the group consisting of a composite product as defined in claim 15.

70. The method of claim 69, wherein at least one of the two layers is produced from a collagen gel containing a mixture of soluble collagen and insoluble collagen, the collagen being selected from the group consisting of type I collagen and Type III collagen.

71. The method of claim 69, wherein said artificial skin comprises living cells obtained from young subjects.

72. The method of claim 69, wherein said artificial skin comprises living cells obtained from elderly subjects.

73. The method of claim 69, comprising living cells selected from the group consisting of fibroblasts, keratinocytes, melanocytes, Langerhans' cells originating from the blood, endothelial cells originating from the blood, blood cells, sebocytes, chondrocytes, osteocytes, osteoblasts, and Merkel's cells, said cells being normal, genetically modified or malignant.

74. The method of claim 73, wherein said blood cells are selected from the group consisting of macrophages and lymphocytes.

75. A method of in vitro testing of the efficacy of a potentially active substance comprising monitoring the effect of said potentially active substance on an artificial skin prepared from a composite product as defined in claim 15, wherein said artificial skin comprises living cells obtained from young subjects.

76. A method of in vitro testing of the efficacy of a potentially active substance comprising monitoring the effect of said potentially active substance on an artificial skin prepared from a composite product as defined in claim 15, wherein said artificial skin comprises living cells obtained from elderly subjects.

* * * * *